Figure 1:
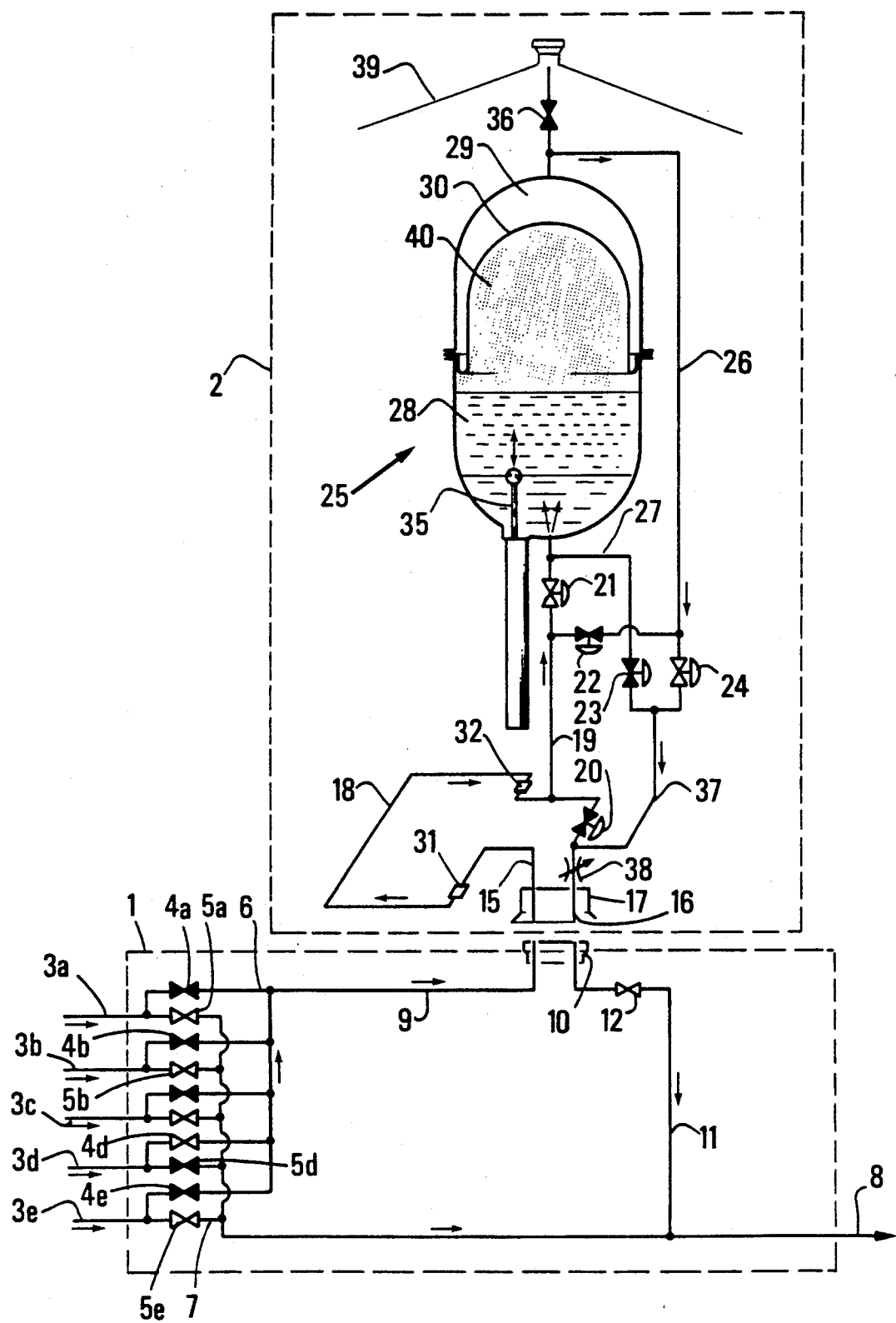

United States Patent [19]

Castel

[11] Patent Number: 5,033,288
[45] Date of Patent: Jul. 23, 1991

[54] METHOD AND DEVICE FOR ANALYZING A MULTIPHASE FLUID FLOWING IN A PIPE

[75] Inventor: Yvon Castel, Croissy sur Seine, France

[73] Assignee: Institut Francais du Petrole, Rueil Malmaison, France

[21] Appl. No.: 441,048

[22] Filed: Nov. 24, 1989

[30] Foreign Application Priority Data

Nov. 23, 1988 [FR] France .................. 88 15236

[51] Int. Cl.⁵ .......................................... G01N 33/28
[52] U.S. Cl. .............................................. 73/61.1 R
[58] Field of Search ...................... 73/61.1 R, 61 R

[56] References Cited

U.S. PATENT DOCUMENTS

| 3,221,541 | 12/1965 | Osborne | 73/61.1 R |
| 3,528,282 | 9/1970 | Stotts, Jr. et al. | 73/61.1 R |
| 4,210,015 | 7/1980 | Euzen et al. | 73/61.1 R |
| 4,215,567 | 8/1980 | Vlcek | 73/61.1 R |
| 4,776,210 | 10/1988 | Baillie et al. | 73/61.1 R |
| 4,813,270 | 3/1989 | Baillie et al. | 73/61 R |
| 4,836,017 | 6/1989 | Bozek | 73/61.1 R X |
| 4,852,395 | 8/1989 | Kolpak | 73/61.1 R |
| 4,924,695 | 5/1990 | Kolpak | 73/61.1 R |

Primary Examiner—Hezron E. Williams
Assistant Examiner—Joseph W. Roskos
Attorney, Agent, or Firm—Antonelli, Terry, Stout & Kraus

[57] ABSTRACT

The method for analyzing a multiphase fluid flowing in a pipe (9, 11, 15, 16, 18) is characterized in particular by the following stages being accomplished:
the flow is drawn off to a sump (28) for the time necessary for it to fill,
once sump (28) is full, said flow is re-started in the pipe (9, 11, 15, 16, 18);
the fluid located in the sump (28) is decanted until the various phases (70, 71, 72) of which the fluid is composed, separate;
a parameter representing the volume of at least one phase is determined by measuring one characteristic sensitive to the variation in the composition of at least two phases of said fluid, and
a macroscopic parameter that gives information on the quality of the fluid as a whole during filling of the sump and before and/or after filling of the sump (28), is monitored.

17 Claims, 3 Drawing Sheets

METHOD AND DEVICE FOR ANALYZING A MULTIPHASE FLUID FLOWING IN A PIPE

The invention relates to a method and device for analyzing a multiphase flowing fluid, particularly an effluent from an oil well to which access is difficult, such as an offshore well or a well in virgin forest.

In general, effluents from oil wells include water, oil, and hydrocarbon gas, each of which has its own phase in the fluid being produced. Petroleum effluents can also include solid materials such as sand.

However, during production in a well, the relative volumes of each fluid phase, and the physical and/or chemical characteristics of the components of these phases such as fluid flowrate, can vary considerably as a function of time.

To adjust the treatment of the fluid or check its operation, it is necessary to find out the quantities and characteristics of the components of these phases. Such treatments may be injection of water containing surfactants or polymers. Moreover, these treatments may include injection of gas (natural gas or $CO_2$) or steam. They may be anticorrosion treatments (corrosion inhibitor added), or treatments to prevent formation of hydrates or deposition of paraffins or salts. These treatments facilitate transport of the fluid or production of oil deposits.

These characteristics are, in particular, the flowrate of the fluid produced by the well, quantitative distribution of the phases of this fluid, and also, particularly for water: resistivity, density, pH, and viscosity; for oil: density, viscosity, electrical conductivity, and thermal conductivity; and for gas: density and molar composition; and for water plus oil: interface tension.

French Pat. No. 1,599,037 describes a process and a device for determining the composition of the fluids produced by an oil well, using a sampling chamber to take a fluid sample, this chamber being lowered into the well. The teaching of this document has the particular drawback of not determining whether the sample taken is representative of the average fluid circulating in the well, of furnishing only a very limited number of measurements, and of being difficult to use in hostile environments, particularly offshore wells.

To overcome these drawbacks, among other things, and more specifically to conduct analyses at the outlets of one or more wells such as oil wells, or in pipes carrying multiphase fluids, the present invention offers a method and an automatic and very reliable device.

The method for analyzing a multiphase fluid flowing in a pipe, according to the invention, is characterized in particular by the following stages:
said flow is tapped off into a sump for the time necessary for filling;
once the sump is full, said flow is re-started in said pipe;
the fluid located in said sump is decanted until the various phases of which the fluid is composed, separate;
a parameter representing the volume of at least one phase is determined by measuring one characteristic sensitive to the variation in the composition of at least two phases of said fluid, and
a macroscopic parameter that gives information on the quality of the fluid as a whole during filling of the sump and before and/or after said filling of the sump, is monitored.

This macrosopic fluid parameter may be the mass of the flowing fluid located in a section of said pipe, for example by using a weighing loop.

Said method can be implemented for different rates of said flow. In an oil well, for example, distribution of the phases or phase components varies according to the flowrate of the fluid.

At least two phases can be sampled, and these samples are sent successively to a set of analyzers through a sampling circuit.

Since certain samples may leave deposits, such as asphaltenes, in the sampling circuit or in the set of analyzers, and these deposits may distort the measurements or clog the circuits or analyzers, it will be advantageous to rinse the sampling circuit and the analyzer set by flushing them with sea water. The sea water may also serve to recalibrate the analyzer set.

To improve this rinsing or decrease the viscosity of the samples, it is possible to heat said sample substance and/or the sea water before making them circulate in the analyzer set.

Knowledge of the output or its variations from a producing oil well is particularly useful for working a deposit since, for example, it allows production of a well to be correctly controlled and its longevity to be ensured. Likewise, for several wells with a common manifold, knowledge of the flowrate of each well allows its production to be optimized. Also, it will be of advantage to measure the time taken to fill a known volume of the reservoir and thus deduce the fluid flowrate. This measure is also applied in long-distance transportation of multiphase fluids where the equipment such as separators can be made ready on time when changes in phase distribution appear, for example when gas plugs occur.

The device for analyzing a multiphase fluid flowing in a pipe, according to the invention, is characterized in particular by having a detector of a macroscopic parameter that gives information on the quality of the fluid flowing as a whole, said detector being disposed in said pipe upstream of a sump designed to sample a quantity of fluid circulating in said pipe, said sump having means for measuring at least one parameter representative of the volume of at least one phase, said pipe having means allowing the fluid to be oriented in said sump.

Said macroscopic parameter detector of fluid quality can be a detector of the mass of flowing fluid located in a section of said pipe.

The device may include a mobile arm located inside said sump, one end of which is designed to sweep at least part of the volume of said sump, the end of the arm having a measuring sensor for one fluid characteristic. Said arm may be moved by a drive element such as a hydraulic jack.

The sensor, measuring one fluid characteristic, may advantageously include a cell generating ultrasound: the fluids analyzed may produce deposits which contaminate the sensor and affect the measurements of the latter.

The use in a sensor of a cell generating ultrasound allows the sensor to be cleaned. For the purpose of cleaning the sensor, it may be advantageous to use ultrasound sensors which also offer the advantage of furnishing useful measurements such as the speed of sound in a fluid or a gas, or the density of the components of one phase, and may allow the components of the phases to be identified.

The device may include a sampling circuit attached to said arm, preferably at the mobile end of the arm which sweeps a large part of the volume of the reservoir, this circuit having a first end terminating at the measuring sensor and a second end feeding a set of analyzers which can be placed outside the sump, in a watertight enclosure filled with gas such as an inert gas, essentially at atmospheric pressure.

The means for measuring a parameter representative of the volume of at least one phase of the fluid may include a sensor measuring another characteristic of the fluid, such as said ultrasonic sensor, and a sensor that detects the position of the arm.

The device may include heating means disposed in the sampling circuit. These heating means may be disposed in the enclosure.

The sump may include a flexible membrane delimiting at least part of the volume of fluid sampled. In this way, it is possible to sample a quantity of fluid at the essentially constant pressure in the pipe and perform sampling in a volume of limited size.

The device may include means for detecting when the sump is full. These means may include a detector of the position of the flexible membrane when it has reached its maximum deformation in the sump, for example when the membrane is applied against a wall of a reservoir containing this sump.

Figure 2:
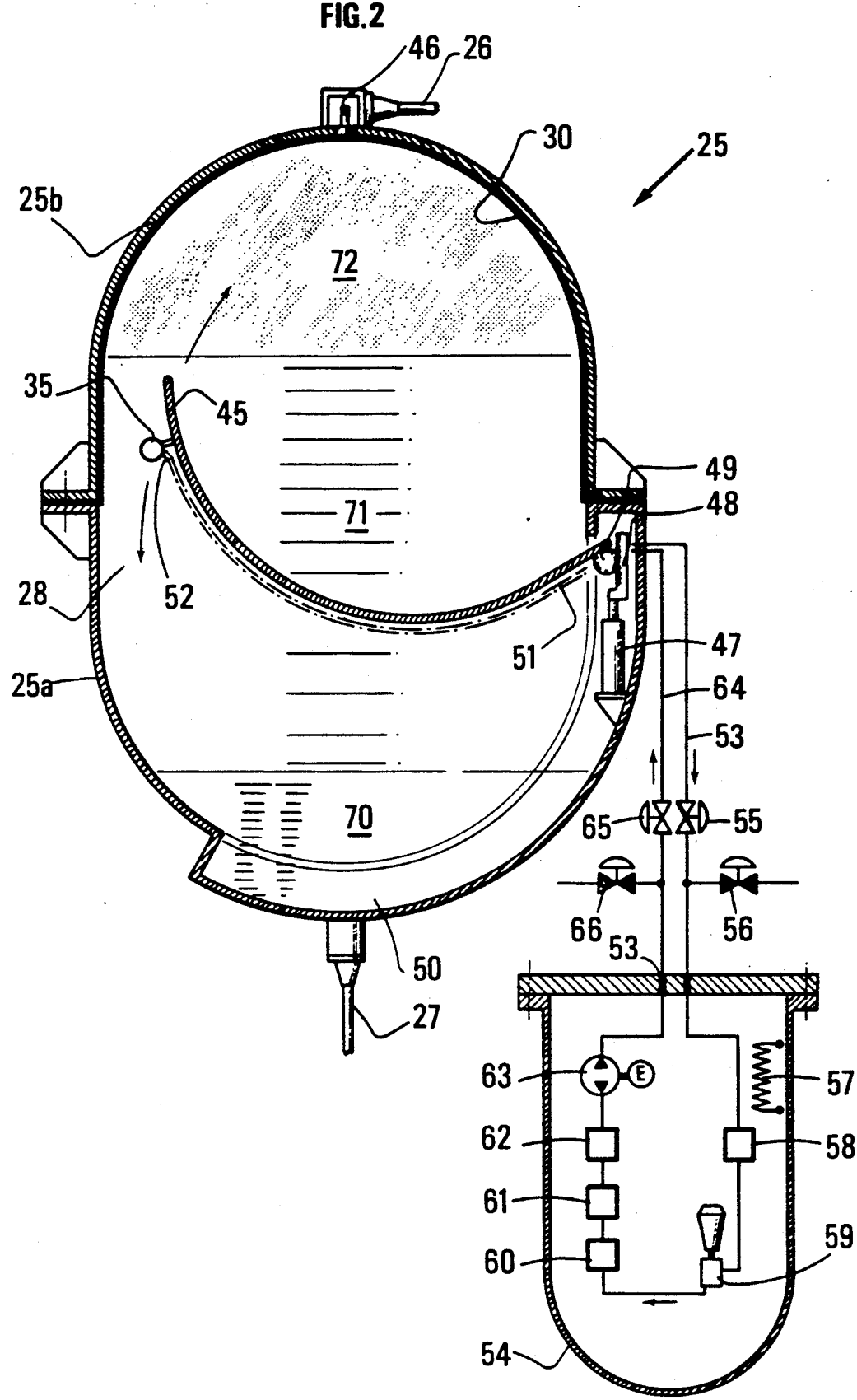
Figure 3:
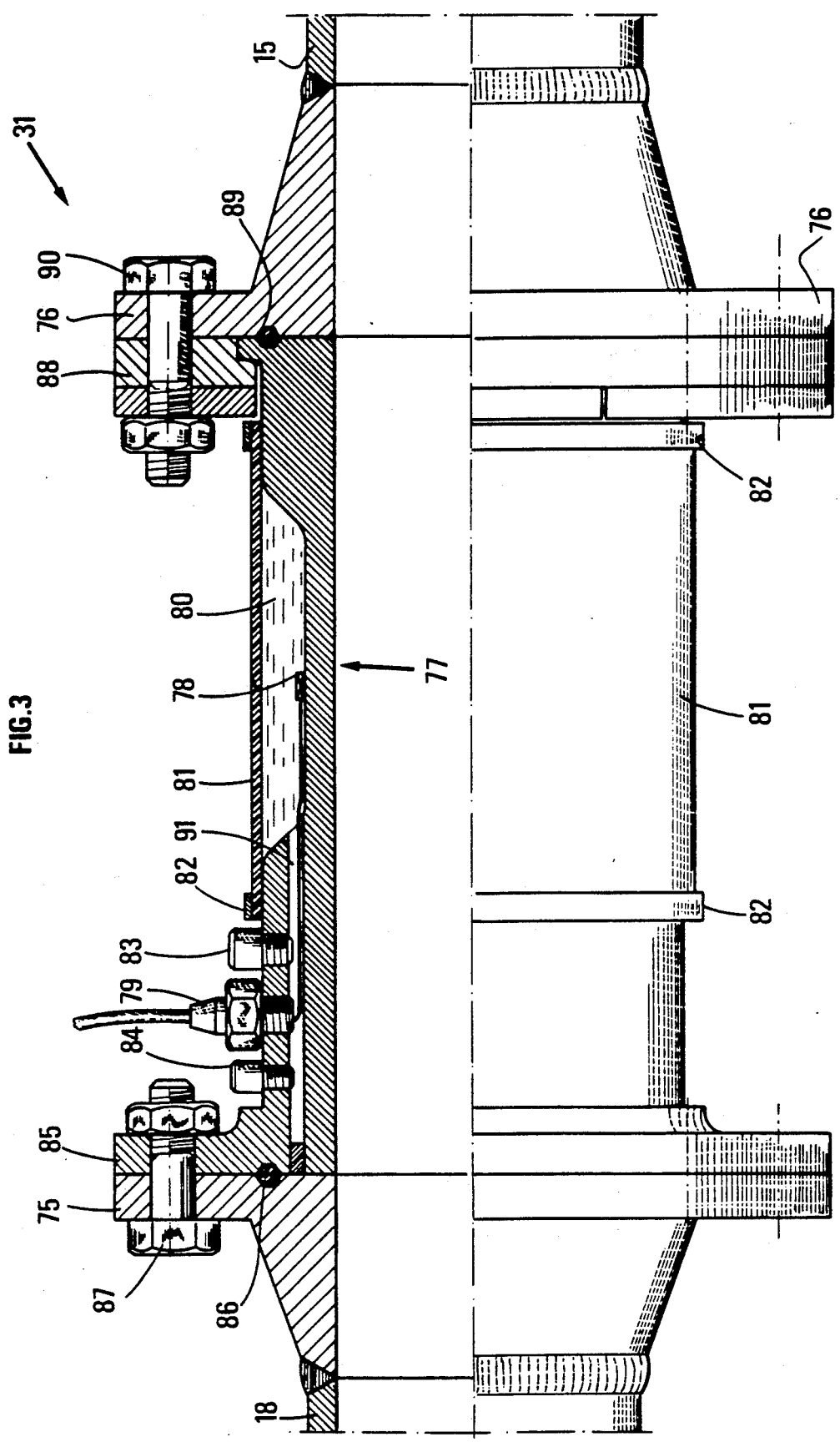

The invention will be properly understood and its advantages will emerge clearly from reading a few sample embodiments illustrated by the following figures, where:

FIG. 1 shows schematically the general layout of the device according to the invention applied to underwater analysis of effluents from several oil wells, FIG. 2 represents a sump and the set of analyzers of a particular embodiment of the device according to the invention, and FIG. 3 shows in detail a sensor in the weighing loop of the device according to the invention which measures the macroscopic parameter of the quality of the flowing fluid.

FIG. 1 shows schematically an underwater analysis station having a base 1 located on the sea bed and a separable module 2 surmounting this base. Base 1 is disposed near several oil wells and is connected to them by lines 3a, 3b, 3c, 3d, and 3e. Each of these lines 3a to 3e ends in two valves, 4a to 4e and 5a to 5e.

Sampling valves 4a to 4e connect to a sampling manifold 6 while valves 5a to 5e connect to a production manifold 7.

Production manifold 7 combines, in a transfer pipe 8, the nonsampled effluents from various wells. By controlling valves 4a to 4e and 5a to 5e, the effluents from the well to be sampled, can be selected. The effluent to be sampled flows through sampling manifold 6, then leaves the manifold via pipe 9 which extends up to the base of a foot connector 10. This foot connector also comprises one end of a pipe 11 for returning the sampled effluents. Pipe 11 rejoins transfer pipe 8 and has an isolation valve 12.

Pipes 9 and 11, ending in the base of foot connector 10 attached to base 1, are extended respectively by pipes 15 and 16 whose ends are disposed in a cap 17 of the foot connector attached to module 2, cap 17 cooperates with base 10 to ensure connection of pipes 15 and 16 with pipes 9 and 11, respectively.

Pipe 15, through which the sampled effluents enter module 2, terminates in the inlet of a densitometric measuring loop 18. The outlet of densitometric loop 18 is connected to a pipe 19 and to a return channel in which is located a return valve 20.

Pipe 19 ends in a sump valve 21 controlling the input of effluents into reservoir 25 and a bypass valve 22 connected to a compensating pipe 26. A pipe 27 closable by a reservoir discharge valve 23 is connected to the pipe connectiong sump valve 21 to reservoir 25.

Reservoir 25 has a sump 28 and an auxiliary sump 29 which are separated from each other by a flexible membrane 30. The sampled effluent is stored in sump 28 and analyzed by probe 35.

Auxiliary sump 29 is connected to compensating pipe 26 and to a vent valve 36 located at the top of auxiliary sump 29.

Compensating pip 26 ends in a compensation valve 24 which connects, like discharge valve 23 connected to pipe 27, to a return pipe 37 connected to pipe 16.

Pipe 16 has an adjustable beam 38 which in particular allows the flowrate of the fluids circulating in densitometric loop 18 to be controlled, either directly when return valve 20 is open or indirectly when auxiliary sump 29 is emptied.

The set of elements in analysis module 2 is protected from material falling from above by a shield 39 which is also designed, because of its cone shape, to collect any contaminating leaks from these elements.

FIG. 1 shows the analysis device during sampling of effluents form well line 3d. For this purpose, the closed valves are drawn in black while the open valves are drawn in white.

To sample effluents from line 3d, valve 5d is closed and valve 4d is opened. The effluents from line 3d pass through pipe 9, densitometric loop 18, pipe 19, and sump valve 21 before entering sump 28 whose volume is initially zero, membrane 30 being applied agains the lower inner wall of the reservoir, i.e. against the common wall of the sump and the reservoir.

The mass of fluid located in densitometric loop 18 is determined by two sensors 31 and 32 which measure the twisting of the loop and, in particular, the variations in twisting due to variations in the weight of fluid traversing loop 18.

Return valve 20, bypass valve 22, and discharge valve 23 are closed. The fluid, which initially fills auxiliary space 29, is drained therefrom by compensating pipe 26 and passes through: compensating valve 24, return pipe 37, adjustable bean 38, pipe 16, isolation valve 12, and return pipe 11, and then flows into transfer pipe 8.

The paths of the effluents from the well to be analyzed and the fluid from auxiliary space 29 are indicated in FIG. 1 by arrows.

When sump 28 is filled, i.e. when its volume is substantially that of reservoir 25, or when the auxiliary space is empty, a sensor that senses the position of membrane 30 closes sump valve 21 and opens return valve 20. Since the volume of sump 28 is known, the time taken for sump 28 to fill is measured, to show the flowrate of the well.

The effluents are stored in sump 28 until sufficient decantation of the various phases of the effluents sampled and performance of analyses by means of telescopic probe 35 have occurred. The probe has indicators of level, density, temperature, pressure, speed of sound, thermal conductivity, and electrical resistivity, so that the different phases can be recognized and characterized, and the effluents can be characterized. The probe, which is initially folded, unfolds according to the height of sump 28, the upper limit of the sump being determined by membrane 30, and returns to its seat, as indicated by arrow 40 in FIG. 1. The measurements are recorded as a function of the travel of probe 35 in sump 28 and, after the results have been processed, allow the characteristics of the various fluid phases to be determined.

When the analysis is complete, valve 21 still being closed, valve 23 is opened, valve 24 is closed, and valve 20 is closed while opening valve 22 to fill auxiliary sump 29 and drain sump 28.

When auxiliary space 29 is filled, i.e. when sump 28 is empty, valves 22 and 23 are closed again, while valve 20 is opened.

Circulation of the effluents during analysis in the sump is then effected in module 2 by densitometric loop 18, return valve 20, bean 38, and pipe 16.

Circulation of the effluents in densitometric loop 18 before and/or after analysis allows the density of the effluents to be monitored and a determination to be made as to whether the effluent sampled is representative, in terms of density, of the effluent arriving via line 3c. This loop 18 also allows the density of the effluents to be monitored over time without it being necessary to analyze them.

To analyze the effluents in another line, valve 4d is closed, valve 5d is opened, and the procedure for this other line is the same as with line 3d.

With no limitation as to the size of the device, the volume of reservoir 25 may be 10 m$^3$ to allow at the same time: a representative analysis of the effluents, a standardized raisable underwater module to be installed in the reservoir, and production of a high-producing well to be absorbed in a reasonable time (10 minutes) on the basis of an average settling time (decanting 10 minutes).

The module may also have a pump to accelerate the filing of sump 28 and thus to allow the behavior of the well to be studied at different flowrates.

Valves 4a to 4e and 5a to 5e can be controlled manually or, better, remote-controlled. Valves 20, 21, 22, 23, and 24 are remote-controlled by an operator or automated by a programmable controller.

Valves 12 and 36 are manual valves. The valves are remote-controlled from an above-water facility such as a production platform. The analysis device also has valves for protection from internal overpressures and underpressures, and safety valves which are not shown in order to simplify the figure.

FIG. 2 shows, in detail, a particular embodiment of the device according to the invention having a set of analyzers 54 external to reservoir 25 and built into the analysis module. The numerical references for the various elements described above have been retained.

Reservoir 25 is made by assembling two cylinders with hemispherical bottoms 25a and 25b, with substantially the same volume. Membrane 30, which is attached at the plane of assembly of the reservoirs, conforms to the upper inside wall of the reservoir when the sump is full, as shown in FIG. 2, and conforms to the lower inside wall of the reservoir when said sump is empty, when retractable arm 45 is withdrawn into the lower bottom of the reservoir.

The top of the reservoir has a proximity detector 46 for the membrane, which alerts the human operator or the automatic system that sump 28 is full. Retractable arm 45 has, at its free end, probe 35 which essentially sweeps the entire height of the reservoir. The arm is moved by jack 47, such as an electrical or hydraulic jack, whose piston has a rack 48 cooperating with a pinion 49 integral with the arm and is nonrotatably mounted.

The shape of arm 45 is such that, once it has retracted into its seat 50, the bottom of the reservoir has no roughnesses that could harm membrane 30 when sump 28 is empty.

To arm 45 is attached part of sampling circuit 51 of which a first end 52 is located near said probe. Second end 53 of this sampling circuit 51 supplies analyzer set 54 disposed in a watertight enclosure pressurized to atmospheric pressure.

The position of the arm is determined by a linear position sensor on jack 47 or an angular position sensor on the arm.

The sampling circuit has a remote-controlled valve 55 and a branch normally closed by remote-controlled valve 56 which is supplied with sea water to rinse the analyzers and the circuits. The analyzers and circuits can also be rinsed with water decanted from the well effluents.

The enclosure protecting the analyzer set has heating means 56, a thermal conductivity analyzer 58, a viscosity analyzer with coaxial cylinders, a pressure and temperature analyzer 59, a vibrating densitometer 60, a pH meter 61, a resistivity analyzer 62, and a sample circulating pump 63.

After analysis, the sample returns via circuit 64 closable by remote-controlled valve 65 and enters sump 28 essentially at first end 52 of circuit 51 and is preferably oriented in a direction opposite that of first end 52. Return circuit 64 has a branch normally closed by remote-controlled valve 66 which allows the rinse water to be discharged into the sea or a sample to be drawn after analysis.

Probe 35, or the measuring sensor, has a cell that generates ultrasound and designed to measure speed of sound or density.

Probe 35, particularly because of the variable frequency of ultrasound emission, is designed to measure the various phases, such as water 70, oil 71, and gas 72. The first end 52 of sampling circuit 51 is disposed near the probe, so that the sample taken is almost identical to that analyzed by probe 35.

Recording of the signals from the probe as a function of the arm position enables the nature and volume of each phase of the effluent sampled in sump 28 to be evaluated.

FIG. 3 shows in detail a sensor 31 in the weighing or densitometric loop of the device according to the invention, such as that of FIG. 1.

In FIG. 1, the omega ($\Omega$) shape of loop 18 allows twist sensors to be positioned at each of its ends to measure the weight of the mass of fluid in the loop. It would have been possible to use other densitometric loop shapes and measure not twisting, but flexion in a section where the shearing force is high or even at a maximum. This would make it possible to measure the deformations in a loop whose ends would be flush-mounted.

Sensors 31 and 32 are disposed at each end of loop 18 which is held only by these two sensors. Sensor 31 is attached to loop 18 and pipe 15 by two API flanges 75 and 76 respectively, welded to loop 18 and pipe 15.

Sensor 31 has, in its central part, a calibrated zone 77 on which are disposed extensometric gauges 78 placed at 45° with respect to the axis of sensor 31, which measure the twisting of the sensor. These gauges are supplemented by longitudinal gauges measuring the vertical flexion of and pull on the sensor, and by transverse gauges measuring the pressure. Article R1820 by Jean Avril in "Techniques de l'Ingenieur," on extensometric sensors, describes the various measuring techniques using electrical extensometric gauges. The gauges are connected to a submersible electrical connector 79 such as a connector manufactured by Souriau et Compagnie, Jupiter, or Deutsch, attached to the wall of the sensor, and which can be connected to the strainmeasuring instruments.

Gauges 78 are protected from the outside environment by an insulating fluid 80 disposed inside a flexible membrane 81, sealed to sensor 31 by using two clamps 82 to mount it on a cylindrical support of the sensor. Fluid 80 is introduced beneath membrane 81 by a filling valve 83 and a drain plug 84.

Sensor 31 has on one side an API 85 flange cooperating with flange 75, a metal-to-metal joint 86 of the BX type, and bolts 87 to ensure immobilization and tightness with respect to measuring loop 18, and on the other side four half-washers mounted in a staggered arrangement to constitute a rotating flange 88, said washers cooperating with a metal-to-metal joint 89 of the BX type and bolts 90 to ensure, without initial twisting, assembly and sealing of sensor 31 on pipe 15.

I claim:

1. A method of analyzing multiphase fluid flowing in a pipe, which comprises the following stages:
   flow of the fluid is tapped off into a sump for the time necessary for filling of the sump;
   when the sump is full, said flow of fluid is reinitiated in said pipe;
   the fluid located in said sump is decanted until various phases of which the fluid is composed, separate within said sump;
   a parameter representing the volume of at least one phase in said sump is determined by measuring one characteristic sensitive to the variation in composition of at least two phases of said fluid in said sump; and
   a macroscopic parameter that gives information on the quality of the fluid as a whole during filling of the sump and before and/or after said filling of said sump is monitored.

2. A method according to claim 1, wherein said macroscopic parameter of the fluid comprises the mass of fluid flowing in one section, including a densitometric loop of said pipe.

3. A method according to claim 1, wherein said method is implemented for different flow rates of said flow.

4. A method according to claim 1, further comprising taking, from at least two phases within said sump, a sample of substance which is sent successively to a set of analyzers through a sampling circuit.

5. A method according to claim 4, further comprising rinsing said sampling circuit and said analyzer set by circulating sea water therethrough.

6. A method according to claim 5, further comprising heating said sample of substance and/or the sea water before passing through the analyzer set, whereby the sea water rinses the sampling circuit of said analyzer set or re-calibrates said analyzer set.

7. A method according to claim 1, further comprising measuring the time required for said sump to fill with said fluid so that the flow rate of fluid in said pipe can be determined.

8. A method according to claim 1, wherein the multiphase fluid comprises effluents of at least one oil well.

9. A device for analyzing a multiphase fluid flowing in a pipe, which comprises detector means for detecting a macroscopic parameter giving information on quality in the flowing fluid as a whole, a sump for sampling a quantity of fluid passing through said pipe, said detector means being located in the pipe upstream of said sump; said sump having means for measuring at least one parameter representing the volume of at least one phase of the fluid; and means for conveying the fluid from said pipe into said sump; said conveying means comprising two different fluid conveying circuits, one for filling the sump and another for emptying the fluid from said sump.

10. A device according to claim 9, wherein said detector means comprising a detector adapted to determine the mass fluid flowing through a section of said pipe.

11. A device according to claim 10, wherein a movable arm is located inside said sump, one of the ends of the arm being arranged to sweep at least a part of the volume of said sump and said end having a sensor for measuring at least one characteristic of the fluid within said sump.

12. A device according to claim 11, wherein said sensor for measuring at least one characteristic of the fluid includes a cell that generates ultrasound.

13. A device according to claim 11, wherein a sampling circuit is attached to said arm, a first end of said coupling circuit terminating at said measuring sensor and a second end of said sampling circuit supplying an analyzer set.

14. A device according to claim 13, wherein heating means are disposed at the second end of the sampling circuit.

15. A device according to claim 11, wherein the means for measuring a parameter that represents the volume of at least one fluid phase comprises a sensor that measures one fluid characteristic and an arm position sensor.

16. A device according to claim 9, wherein said sump is located within a reservoir having a flexible membrane that delimits at least a part of the fluid sampled into said sump.

17. A device according to claim 16, wherein said reservoir has means that detect when said sump is filled with said fluid.

* * * * *